United States Patent

Jambo et al.

[11] Patent Number: 5,858,204
[45] Date of Patent: Jan. 12, 1999

[54] ELECTROCHEMICAL SENSOR AND PROCESS FOR ASSESSING HYDROGEN PERMEATION

[75] Inventors: Hermano Cezar Medaber Jambo; José Antônio da Cunha Ponciano Gomes, both of Rio de Janeiro, Brazil

[73] Assignee: Petroleo Brasileiro S.A.:Petrobras, Rio de Janeiro, Brazil

[21] Appl. No.: 615,885

[22] Filed: Mar. 14, 1996

[30] Foreign Application Priority Data

Mar. 14, 1995 [BR] Brazil .............................. PI 9501061-0

[51] Int. Cl.⁶ .................................................. G01N 27/26
[52] U.S. Cl. ........................ 205/775; 204/400; 205/790.5
[58] Field of Search .................................. 204/400, 404; 205/775, 775.5, 776, 776.5, 777, 790.5

[56] References Cited

U.S. PATENT DOCUMENTS

| | | | |
|---|---|---|---|
| 2,886,497 | 5/1959 | Butler | 205/790.5 |
| 3,629,090 | 12/1971 | Ghormley | 204/404 |
| 3,798,755 | 3/1974 | Sandstrom | 204/272 |
| 4,065,373 | 12/1977 | Martin et al. | 204/195 |

FOREIGN PATENT DOCUMENTS 2218520 of 1989 United Kingdom .

WO8303007 9/1983 WIPO .

OTHER PUBLICATIONS

Corrosion 84, Paper No. 237, "Corrosion Monitoring with Hydrogen Probes in the Oil Field" by William H. Thomason, 13 pages.

Corrosion 91, Paper No. 444, "Electrochemical Noise for Detection of Susceptibility to Stress Corrosion Cracking" by E.A. Eden, et al., 13 pages.

Primary Examiner—T. Tung
Attorney, Agent, or Firm—Sughrue, Mion, Zinn, Macpeak & Seas, PLLC

[57] ABSTRACT

An electrochemical sensor designed to be employed in equipment of petrochemical plants made of an electrochemical cell without polarization which includes an outer tube or first electrode and an internal rod or second electrode. Both first and second electrodes being provided with wires for external electrical contact. The first and second electrodes being separated by a standard electrolytic solution for the oxidation of the nascent hydrogen which is generated by the corrosion reactions caused by sulfur compounds in contact with the hydrogen-permeable metal which constitutes the equipment of petrochemical plants. The sensor is coupled to a zero resistance ammeter which assesses the electrical current generated by the oxidation of the nascent hydrogen and provides a plot of electrochemical noise.

14 Claims, 3 Drawing Sheets

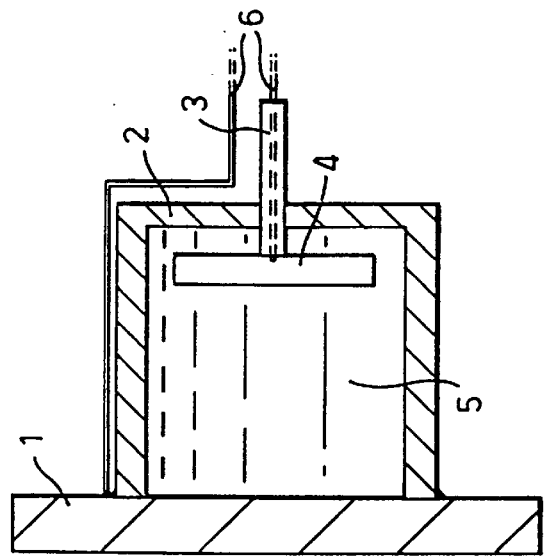
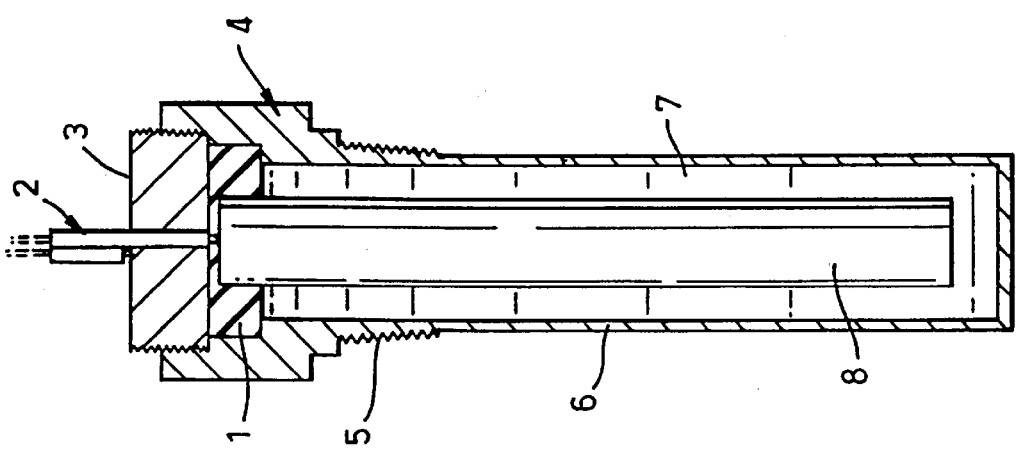

_____
ELECTROCHEMICAL SENSOR AND PROCESS FOR ASSESSING HYDROGEN PERMEATION

FIELD OF THE INVENTION

1. Background of the Invention

This invention relates to an electrochemical sensor and to a process for assessing the permeation of the hydrogen which is absorbed by the metal walls of the process equipments used in the chemical and petrochemical industries. More specifically, the present sensor and process assess the hydrogen permeation by combining an electrochemical cell without polarization and a simple circuit based on the technique known as zero resistance ammetry (ZRA).

In the petrochemical industry the main corrosion agent which generates hydrogen and damages the metals which constitute the equipments is hydrogen sulfide $H_2S$ from the feed or generated during the refining from the decomposition of sulfur compounds such as mercaptans, sulfur organic acids and elemental sulfur. The decomposition of hydrogen sulfide in the presence of water generates hydrogen ion $H^+$, which is reduced on the surface of the metal which makes up the structure of the equipment, by acquiring an electron and neutralizing its charge. The trend of the hydrogen to penetrate the metal is a function of various electrochemical parameters such as pH and partial pressures of $H_2$ and $H_2S$ among others. The penetration of hydrogen into the metal of the equipment generates various kinds of damages, the final result being cracking and fractures which eventually lead to the discarding of the equipment, with the consequent economic loss and reduction in industrial safety.

Thus, the real time monitoring of the decay observed in materials used in industrial plants is presently seen as essential to the economical operation and maintenance of process equipment. Aiming at establishing a prevision of the corrosion rates and internal damages caused in steels used in the construction of equipments, various devices have been developed directed to the monitoring of the hydrogen generated and absorbed in containers and pressure vessels. These devices are instruments which can be used to assess the hydrogen which is generated by corrosion reactions and other processes.

2. Prior Art

W. H. Thomason in Paper no 237 of CORROSION 84, April 1984, Louisiana, U.S.A., cites that the losses caused by the substitution of highly priced equipment added to the production loss, as well as the savings earned through the improvement in corrosion control lead to the need that the procedures used in the corrosion control provide for a quick assessment of the corrosion rates, if possible in real time. The hydrogen sensor is a device for effecting corrosion experiments which conform to said need. In the oil industry, there are three kinds of hydrogen sensors currently used: under pressure, under vacuum and electrochemical.

The hydrogen sensor which is operated under pressure works by assessing the hydrogen pressure which accumulates in a sealed cavity. In the most common type, a small steel tube has one end sealed while the other end is provided with a pressure monitor. A rod can be inserted within the tube to reduce the internal volume and increase the sensitivity of pressure to the entrance of hydrogen. The sensor is to be placed on the external surface of the tubes or within vessels.

The hydrogen sensors which operate under vacuum use reduced pressure within the cavity into which hydrogen is permeated. A magnetic ion pump keeps the system under vacuum, the electrical current requisite of such pump being proportional to the rate at which hydrogen is captured by the pump. This is an expensive and complex probe, its use being more suited to laboratory scale.

The electrochemical sensor is also based on a cavity into which hidrogen permeates. The cavity contains an electrolyte in which is inserted an auxiliary electrode which oxidises the hydrogen atoms which enter the cavity. The current produced by the sensor is the sum of the current which is necessary to keep the proper anodic potential and the current which is necessary to oxidise the entering hydrogen atoms. Among the existing electrochemical sensors, one employs concentrated sulfuric acid as the electrolyte and a palladium film as the anode. Another one uses an electrolyte made up of diluted sodium hydroxide, the steel surface which contacts the electrolyte serving as the anode in the electrochemical reaction. Here, the steel surface where hydrogen is oxidised is immersed in a 0.1 to 0.2M NaOH solution, an oxidising potential comprised between zero and 0.4 V (vs a callomel-satured electrode) being applied to the steel surface. The hydrogen atoms permeate through the steel, reach the electrolyte/steel interface and are oxidised to form $H^+$ ions which enter the solution. The current required to run the reaction assesses the number of hydrogen atoms which emerge from the steel.

The electrochemical probe made up of nickel oxide uses as the source of oxidising current a nickel oxide electrode similar to those used in nickel-cadmium batteries. The probe based on nickel oxide consists of a chamber which contains an electrolyte, which is made to contact the steel surface, the nickel oxide electrode being inserted in the interior of the chamber. When the circuit between the nickel oxide electrode and the steel surface is completed the current is assessed and used as an indication of the hydrogen permeation rate. Generally speaking, the devices used to assess corrosion employ separated electrodes and are immersed in the same electrolyte, as taught for example by D. A. Eden et al. in CORROSION 91, Paper no 444 on page 10. As can be seen on the scheme described in this paper, as well as in other papers of the prior art, there are two or three electrodes.

It should be pointed out that all of the electrochemical sensors of the state-of-the-art are polarized, either through electronic means or galvanic polarization, that is, metal-oxide couples.

On the other hand, the assessment of electrochemical phenomena is usually effected with the aid of instruments called Zero Resistance Ammeters (ZRA). Such instruments make possible that the assessment of the current circulating between two metallic electrodes immersed in a conducting solution or electrolyte be effected by coupling said current to the ZRA without the need to introduce an electrical resistance. One application of the ZRA in electrochemical measurements is described in GB-A-2218520 where the corrosion rates of various metals made to contact an electrolyte are assessed by means of a device which comprises a potentiostat connected to a reference electrode and an auxiliary electrode, both electrodes localized in the electrolyte and a zero resistance ammeter for each metal.

However, the present sensors used for the monitoring of hydrogen show various drawbacks which arise either from the very principle on which they are based, for example, the sensors which work under pressure or vacuum, or from the way they are built, as the electrochemical sensors which employ potentiostats and metallic films of palladium or nickel, which are costly and where electrodeposition is difficult.

Thus, there is still the need of an electrochemical sensor, without polarization and easy to built and use in the field which can be attached either to the interior or the externals of petrochemical equipments, and over all, which can do without potentiostats, reference electrodes or polarization through galvanic couple, that is, expensive and wearing out electrodes. Additionally, in the desirable electrochemical sensor, such as that described and claimed in the present invention, the electrical current generated by the electrons from the hydrogen ion oxidation can be read with the aid of a simple circuit which is equivalent to a zero resistance ammeter (ZRA).

SUMMARY OF THE INVENTION

The present invention deals with an electrochemical sensor for hydrogen designed to monitor the hydrogen attack to equipment used in the petrochemical industries, the sensor comprising a metal portion for hydrogen permeation which contains an electrochemical cell without polarization and an electronic unit which provides figures for readings. The present invention deals also with the process for assessing the permeation of the hydrogen generated in corrosion reactions using the electrochemical sensor herein described and claimed.

In the present sensor, the metal portion which contains the electrochemical cell without polarization is made up of an outer tube made of carbon steel or other metal of which it is desired to determine the hydrogen permeation and which works as the first of two electrodes, a tube or internal rod of the same material and which works as the second of the two electrodes, an internal electrolyte, insulating materials and wires for electrical connection, the outer and internal tubes (the electrodes), electrolyte and electrical connections making up the electrochemical cell. Both electrodes are connected to a zero resistance ammeter in order to assess the electrical current generated by the oxidation of the nascent hydrogen produced by the corrosion of the steel of the outer tube—first electrode—when exposed to the process fluid. Contrary to the electrochemical devices using ZRA of the prior art, where two or more electrodes are immersed in the same corrosive medium, in the present invention one of the two electrodes (outer tube) is exposed to the corrosive medium and the other one (internal tube or rod) is immersed in a standard electrolytic medium. Both electrodes are electrically connected while the media (the corrosive medium and the electrolytic medium) are not connected.

The construction of the electrochemical sensor of the present invention is based on the building up and permeation of the hydrogen generated by the corrosion reactions of the outer tube when this tube is exposed to a corrosive medium.

The so-generated hydrogen is reduced on the external surface of the outer tube and diffuses through the wall of same tube as atomic hydrogen. When such hydrogen contacts the alkaline solution of the electrochemical cell—the standard electrochemical medium—in the interior of the sensor, it is oxidised to hydrogen ion with the release of an electron. The electron release generates an imbalance between the surfaces in contact with the electrolyte since these surfaces work as two passive electrodes which are electrically connected. The electrical current generated by the contact of hydrogen with the internal surface of the external electrodes can be read with the aid of a zero resistance ammeter.

The zero resistance ammeter used in the present invention makes direct readings of the equilibrium currents between the two electrodes of the electrochemical cell. The electron which is generated by the permeation and oxidation of the hydrogen is immediately read in the ammeter as an electrical current. Also, the technique of the zero resistance ammetry can be applied in studies of electrochemical noise. Instantaneous values of current can be read and related to time.

Therefore, one objective of the present invention if a low-cost, high-efficiency electrochemical sensor of which the electrochemical cell, being devoid of polarization, dispenses with the use of a potentiostat, sacrifice metal oxides as second electrode as well as special coatings to be applied on the first electrode, such as coatings made of Ni or Pd.

Another objective is an electrochemical sensor made up of an electrochemical cell devoid of polarization and an electronic portion, designed to assess, also with the aid of the technique of electrochemical noise, the hydrogen which is permeated through the walls of the electrochemical cell of the sensor, the hydrogen assessment being then related to the internal damage produced in the equipment.

Still another objective is an electrochemical sensor which can be placed either internally or externally to the equipment of which corrosion is to be assessed, the corresponding electronical reading being made at a distance from the equipment.

A further objective is to couple the electrochemical sensor to an electronic relay which triggers a signal once is attained a certain amount of permeated hydrogen, this amount being considered deleterious to the equipment, so that corrections can be effected in the operation parameters of the equipment being monitored.

BRIEF DESCRIPTION OF THE DRAWINGS

FIG. 1 represents a cut view of the sensor of the present invention.

FIG. 2 is a modification of the sensor of the present invention designed to be applied externally to the process equipment.

PREFERRED MODES

Figure 3:
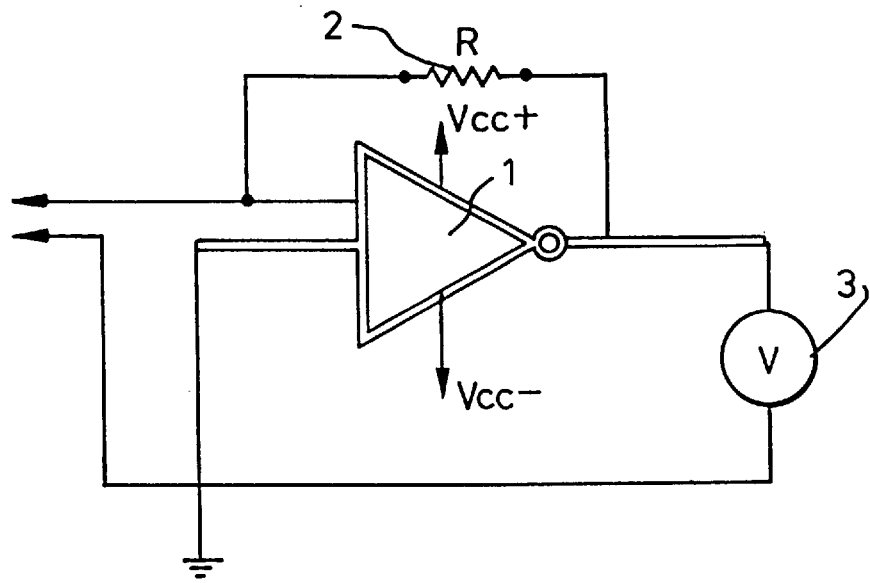
FIG. 3 is a scheme of the zero resistance ammeter which together with the electrochemical cell devoid of polarizaiton makes up the electrochemical sensor of the present invention.

Basically the present invention contemplates two preferred modes, one of which as illustrated in FIG. 1, where the electrochemical sensor is placed internally to the equipment of which the corrosion caused by hydrogen is being assessed, this being called the "insertion mode". Another mode is illustrated in FIG. 2, where the electrochemical sensor is made to adhere to the outer wall of the equipment of which the corrosion caused by hydrogen is being assessed.

In both modes, the sensor of the present invention is basically made up of a metallic portion which contains an electrochemical cell, and an electronic portion. As illustrated in FIG. 1, the metallic portion of the insertion mode of the sensor of the present invention comprises:

Outer Tube

This is a machine-made steel tube (6) which works as the first of two electrodes. It is in this tube that the corrosion reactions in the medium where the hydrogen permeation is to be assessed occur. The width of the wall of the outer tube can vary according to the aggressivity of the corrosion agents and to the pressure of the medium. The length and the diameter of the outer tube can be varied depending on the place the outer tube will be used as well as on the expected duration of the tube. Typical values are 18 mm diameter and 80 mm length. Outer tube (6) can be externally weld to the body of the device or either be integral to the equipment. The sensitivity of the sensor of the invention can be set as a function of the outer tube thickness, a reduction in thickness implying in sensitivity increase. For better results, the metal of which is made up the outer tube (6) is preferably the same as the metal of the equipment of which the corrosion process is to be assessed.

Outer Body

This section of the equipment is designed as (4) in FIG. 1 and can be an integral part of outer tube (6); for field installation it presents a screwed region (5). NPT screws can be used.

Electrolyte Solution

This is an alkaline solution (7) of 1 to 3N analytical grade NaOH free of chloride ions where atomic hydrogen which permeated the wall of the outer tube (6) is oxidised. This electrolyte can be buffered or not, according to the expected duration of the sensor. In order to ease the replacement of spent electrolyte used horizontally in the field, the electrolyte is soaked in cellulosic stuff. In spite of the fact that various electrolytes can be used, NaOH is the preferred one since the passivation area of steel in NaOH is extended. The electrochemical potential of iron in a NaOH environment favors the oxidation of hydrogen, which does not necessarily occur in other media.

Internal Rod

Internal rod (8), which can be a tube or rod, is the second electrode through which is made the reading of the electrical current. Diameter and length of internal rod (8) conform to the dimensions of the outer tube (6). It is recommended that those areas of the internal surface of the outer tube (6) which are exposed to the electrolyte and the outer surface of the internal rod (8) be the same. Their surface should be ground as well as the internal surface of the outer tube (6). The metal which makes up the internal rod (8) can be the same or similar steel as that employed in the outer tube (6).

Isulating Material

Insulating material (1) electrically insulates the two electrodes, outer tube (6) and internal rod (8), so as to avoid any direct contact between the two electrodes.

Metal Threaded Disc

This disc (3) fastens the electrodes and seals the electrolyte. It can be threaded (preferably a thin thread) or either another fastening means can be used. Electrical wires are provided within disc (3) in order to provide figures for asssessing the hydrogen permeation.

Wire for Electrical Contact

There are two wires (2), one for each electrode. The way to separate the wires comprises passing a wire through the threaded disc (3) and weld the wire on the internal rod (8); the other wire is directly welded on the threaded disc (3) or to the outer body (4) by some fastening means such as welding, or a fastening screw. The welding or fastening of the wire to the internal rod (8) should be electrically insulated from the electrolyte.

FIG. 2 illustrates the second preferred mode of the invention, whereby the electrochemical sensor is externally placed to the equipment of which the corrosive process is to be assessed. According to this mode, the electrochemical sensor comprises an outer container (2) coupled to the plate of the industrial equipment (1) which is under study, the wall of equipment (1) working as one of the two electrodes of the electrochemical cell, a metallic disc (4) as the second electrode, electrical connection (6) used for reading the current and insulated from the outer container (2) by an insulating material (3) and electrolyte (5) made up of a 1 to 3N NaOH solution. The building material used for the outer container (2) is not relevant to the desired assessment of the corrosion levels.

The electronic portion of the electrochemical sensor of the present invention comprises a zero resistance ammeter built from a commercial amplifier. With this instrument direct readings of the equilibrium currents can be obtained between the two electrolytes of the electrochemical cell of the sensor. As soon as hydrogen permeates and oxidises, the electron which is generated is immediately read as electrical current at the ammeter. The present process makes equally possible to apply the technique of electrochemical noise. Instantaneous measurements of current can be determined and related to time. As stated before in the present specification, the main difference between the use of ZRA in the conventional electrochemical noise technique and the present invention is that in the state of the art both electrodes are immersed in a corrosive medium, while in the present invention there are two electrodes immersed in an electrolyte which is the alkaline solution, this solution being separated from the corrosive medium. FIG. 3 shematically illustrates the ammeter of the present invention. Therefore, the ammeter of the present invention which coupled to the electrochemical cell of the metallic portion constitutes the inventive sensor can do without the use of any kind of metallization using noble metals, as well as oxide-based electrodes, or even reference counter-electrodes.

Still according to FIG. 3, the zero resistance ammeter of the present invention uses a commercially available operational amplifier (1) and a +15V–15V source. Voltmeter (3) should be of high impedance and preferably should operate in the digital mode. The wires for the metallic portion of the sensor of the present invention are attached according to FIG. 2. Resistor (2) can range from 1 KOhm to 1 MOhm depending on the desired sensitivity at the reading and on the characteristics of the amplifier. The benefit of the amplifier will be defined by the resistor.

The plot obtained by the zero resistance ammeter of the present invention in using the technique of electrochemical noise is called "signature" of the corrosion process, since the plot or signature obtained vary if the current is produced by the corrosion of the steel of which is made the equipment or either by the oxidation of hydrogen, that latter being what is desired to assess. In the present invention, an unexpected advantage is that, contrary to the sensors of the state of the art, in the absence of potentiostat, the technique of electrochemical noise makes possible to work without outer electrochemical polarization, which brings undesirable troubles such as the generation of electronical noise. For sensors which use a potentiostat, there is the need to employ palladium or nickel films which protect the steel and do not hinder the reoxidation of hydrogen. The potentiostat used in the sensors of the state of the art cause interferences into the medium, by polarizing the coated steel as related to the reading medium. The potentiostat applies a potential and assesses current; however, current alterations can occur caused by parameters other than hydrogen oxidation, these alterations being read by the potentiostat. Further, the potentiostat requires a third electrode placed within the system, this being a potential source of problems in the field.

The present invention provides for another advantage which is the indirect assessment of the actual damage caused by the hydrogen which is blocked within the walls of the equipment. A portion of the hydrogen which is generated is blocked within the walls of the equipment in view of the fact that in general, steels contain inclusions of manganese sulfides, oxides and other stuffs which constitute preferred targets for hydrogen attack. According to the present invention, it is possible to assess the amount of internal hydrogen Q internal and the amount of external hydrogen Q external through the use of an internal sensor and an external sensor. The thin wall of the internal sensor permeates all the hydrogen which is produced, while the wall of the equipment to which is coupled the external sensor retains a portion of the hydrogen. Thus, the internal and external sensors will provide an assessment of electrochemical noise corresponding to different amounts of hydrogen, the difference between the internal amount of hydrogen and the external amount corresponding to the hydrogen retained within the walls of the equipment.

Since the amplifier of the present invention is a standard integrated circuit it is possible to design several electronic circuits. The circuit works so as to amplify the current so that the resistance values do not interphere in the reading to be effected on the current. The reading obtained for the potential is mathematically converted into electrical current which in turn is directly proportional to the hydrogen flow which reaches the measuring device. The amplifier of the present invention can be directly connected to a board for data acquisition inserted in a personal computer or to a commercial voltmeter or either be connected to a plotter. The device employing a personal computer leads to a plot, including the figure of actual damage mentioned hereinbefore. Another possibility for the reading of the current is to install an alarm so that beyond a certain amount of current an alarm is triggered from an electronic relay, so that the operation staff can take the necessary steps to lessen the hydrogen activity.

The present invention will now be illustrated by the following Example, which should not be construed as limiting same.

EXAMPLE

Figure 4:
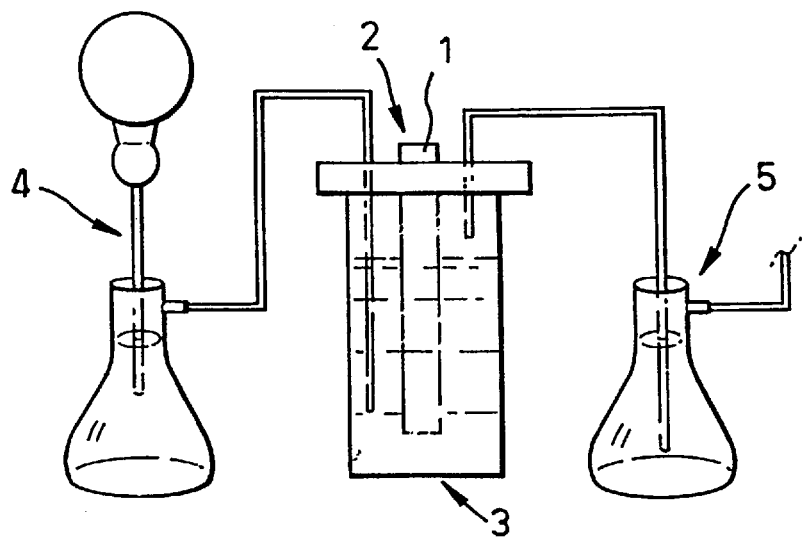
FIG. 4 illustrates a hydrogenation scheme for a test of the electrochemical sensor of the present invention, according to EXAMPLE 1.

This Example illustrates the use of the electronic sensor of the present invention according to the internal or insertion mode. FIG. 4 shows a scheme for acquiring data as described hereinafter. A cylindrical acrylic cell (3) having 13.3 cm internal diameter and 11.2 cm height represents a refinery equipment. The electrochemical sensor (2) is vertically positioned in the center of the cell, said cell being replenished with the hydrogenating solution, H2S being continuously bubbled throughout cell (3). The effluent H2S is neutralized by means of a NaOH solution. The feeding modulus for sensor (1) is externally assembled and coupled to the instruments for signals acquisition and analysis. In order to register the sensor response, equipments for data acquisition and a computer-controlled signal digital analyzer Hewlett Packard 3562 were used. The response signal from the sensor was analyzed after passage through a Notch filter having cut frequency at 60 Hz (80 db/decade) and a lower-limit filter having cut frequency at 10 Hz. The analyzed signals were obtained in the domains of time and frequency, after a treatment effected by the analyzer.

The hydrogenation solution is prepared according to TM 0177 standard of the National Association of Corrosion Engineers (NACE, U.S.A.). The hydrogenating solution was modified in order to be free of chloride and buffered with sodium acetate. The concentration of choice was 1M acetic acid +1M sodium acetate. Saturation with H2S was kept as such, while the solution was not deaerated. H2S was generated in a separate reservoir, according to FIG. 4, connected to the cell through a system of valves and conduits, H2S being generated in flask (4) from the reaction between iron sulfide and sulfuric acid:

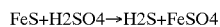

FeS+H2SO4→H2S+FeSO4

Figure 5:
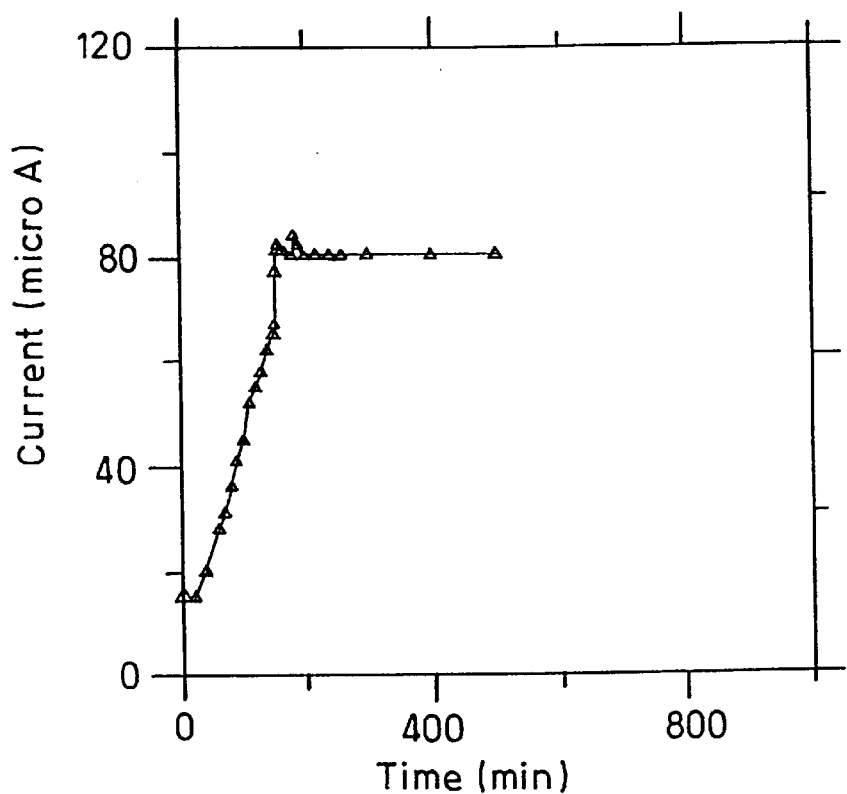
FIG. 5 illustrates the response of the electrochemical sensor at the beginning of the hydrogenation, as described in EXAMPLE 1.

According to FIG. 5, after nearly 30 minutes of H2S bubbling there is an increase in the signal which corresponds to the current generated by the oxidation of hydrogen in the 3N NaOH electrolytical solution stored in the interior of the electrochemical cell of the sensor.

Figure 6:
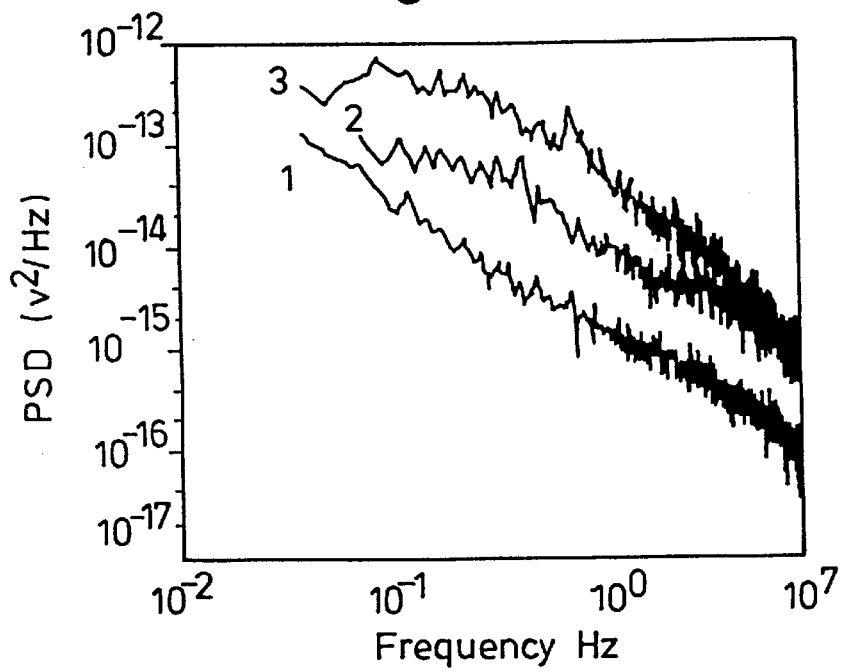
FIG. 6 illustrates the Power Spectral Density of the stationary current figures as assessed by the electrochemical sensor of the present invention, as described in EXAMPLE 1.

As illustrated on FIG. 6, spectral analysis can be used for hydrogen detection when using the electrochemical sensor of the present invention. According to FIG. 6, the Power Spectral Densities of the current variations can be obtained in the stationary states in the presence as well as in the absence of hydrogen, these data being illustrated in a plot typical of a phenomenon known as ELECTROCHEMICAL NOISE, where curve 1 represents the Power Spectral Density (PSD) of the stationary values of current assessed in the absence of hydrogen, curve 2 the PSD in the beginning of the hydrogenation stationary state and curve 3, PSD after 24 hours hydrogenation.

We claim:
1. An electrochemical sensor for assessing the permeation of hydrogen generated by the corrosion of hydrogen-permeated metal by a process fluid used in petrochemical equipment, the electrochemical sensor comprising:
   an electrochemical cell without polarization comprising
      an outer body comprising a first electrode which is in contact with the process fluid and which is made of a hydrogen-permeable metal,
      an electrolytic solution isolated from said process fluid by said first electrode, and
      a second electrode of the same material as said first electrode in contact with the electrolyte solution and insulated from the outer body;
   a zero resistance ammeter for assessing the electrical current generated by the oxidation of nascent hydrogen produced by the corrosion of the hydrogen-permeable metal when the first electrode is exposed to the process fluid; and
   wires connecting each of the first and second electrodes to the zero resistance ammeter.
2. An electrochemical sensor according to claim 1, suitable for insertion into the equipment exposed to the process fluid,
   wherein said first electrode is comprised of an outer tube,
   wherein said second electrode is comprised of an internal rod, and
   said electrolyte solution being adapted for oxidizing nascent hydrogen, said first and second electrodes being separated by the electrolyte solution, and said second electrode being insulated from the outer body by means of an insulating and sealing stock and a screwed metallic disc.
3. An electrochemical sensor according to claim 2, wherein the electrolytic solution is an alkaline solution.
4. An electrochemical sensor according to claim 3, wherein the alkaline solution is made up of a 1 to 3N NaOH solution free of chloride ions.

5. An electrochemical sensor according to claim 2, wherein an outer surface of the internal rod and an internal surface of the outer tube comprise metal surfaces.

6. An electrochemical sensor according to claim 5, wherein said metal surfaces comprise the same machined surface finish.

7. An electrochemical sensor according to claim 1, to be used externally to the equipment, which is exposed to the process fluid, wherein:

said outer body is attached to a wall portion of the equipment which is exposed to the process fluid, said wall portion comprising said first electrode, said electrolyte solution being adapted to oxidize the nascent hydrogen, said first and second electrodes separated by the electrolyte solution, and said second electrode being insulated from the outer body by means of insulating stock.

8. An electrochemical sensor according to claim 1, wherein the zero resistance ammeter is physically apart from the body of the sensor by a distance of 100 meters or more.

9. An electrochemical sensor according to claim 1, wherein the signal of the zero resistance ammeter can be utilized by other signal analyzing equipment for triggering correcting procedures for the process.

10. A process for assessing hydrogen permeation with the aid of the electrochemical sensor according to claim 1, wherein nascent hydrogen generated by the corrosion reaction of the hydrogen-permeable metal constituting the petrochemical equipment permeates the first electrode of the sensor and is oxidized in contact with the electrolyte solution so as to generate a free electron which is turned into electrical current which is read by the zero resistance ammeter coupled to the sensor.

11. A process according to claim 10, wherein the zero resistance ammeter reads the current as an electrochemical noise signal.

12. A process according to claim 11, wherein a plot obtained by the zero resistance ammeter of the signature of the electrochemical noise relates solely to the electrons which are generated in the oxidation of the permeated hydrogen.

13. A process according to claim 10, wherein the zero resistance ammeter reads an electrical current as a DC value.

14. An electrochemical sensor according to claim 1, wherein said second electrode is isolated from the process fluid.

* * * * *